(12) United States Patent  
Yang et al.

(10) Patent No.: US 8,075,854 B2  
(45) Date of Patent: Dec. 13, 2011

(54) MICROFLUIDIC CHIPS FOR RAPID MULTIPLEX ELISA

(75) Inventors: Shang-Tian Yang, Dublin, OH (US); Yunling Bai, Cockeysville, MD (US); Wei-Cho Huang, Columbus, OH (US)

(73) Assignee: The Ohio State University Research Foundation Bioprocessing Innovative Company

( * ) Notice: Subject to any disclaimer, the term of this patent is extended or adjusted under 35 U.S.C. 154(b) by 604 days.

(21) Appl. No.: 11/937,001

(22) Filed: Nov. 8, 2007

(65) Prior Publication Data

US 2009/0123336 A1    May 14, 2009

(51) Int. Cl.
*G01N 30/00* (2006.01)
(52) U.S. Cl. .... 422/503; 422/417; 422/68.1; 435/287.2; 435/287.1; 435/7.92; 436/501; 436/518
(58) Field of Classification Search ................. 422/68.1; 435/6, 287.2
See application file for complete search history.

(56) References Cited

U.S. PATENT DOCUMENTS

| | | | | |
|---|---|---|---|---|
| 6,103,199 | A * | 8/2000 | Bjornson et al. | 422/100 |
| 6,610,499 | B1 * | 8/2003 | Fulwyler et al. | 435/7.1 |
| 2002/0127740 | A1 * | 9/2002 | Ho | 436/518 |
| 2002/0176807 | A1 * | 11/2002 | Gubernator et al. | 422/102 |
| 2002/0187564 | A1 * | 12/2002 | Chow et al. | 436/518 |
| 2003/0027352 | A1 * | 2/2003 | Hooper et al. | 436/169 |
| 2003/0152934 | A1 * | 8/2003 | Chang et al. | 435/6 |
| 2003/0190608 | A1 * | 10/2003 | Blackburn | 435/6 |
| 2005/0097951 | A1 * | 5/2005 | Hasselbrink et al. | 73/253 |
| 2005/0277125 | A1 * | 12/2005 | Benn et al. | 435/6 |
| 2006/0286549 | A1 * | 12/2006 | Sohn et al. | 435/5 |
| 2007/0042427 | A1 * | 2/2007 | Gerdes et al. | 435/7.1 |
| 2007/0122819 | A1 * | 5/2007 | Wu et al. | 435/6 |
| 2008/0273918 | A1 * | 11/2008 | Linder et al. | 403/31 |
| 2009/0079976 | A1 * | 3/2009 | Cunningham et al. | 356/246 |

OTHER PUBLICATIONS

Bai et al., "Surface Modification for Enhancing Antibody Binding on Polymer-Based Microfluidic Device for Enzyme-Linked Immunosorbent Assay", *Langmuir*, 2006, 22, 9458-9467, American Chemical Society.

Call et al., "Detecting and genotyping *Escherichia coli* O57:H7 using multiplexed PCR and nucleic acid microarrays", *International Journal of Food Microbiology*, 67 (2001) 71-80, Elsevier Science B.V.

Carbonaro et al., "A resistive-pulse sensor chip for multianalyte immunoassays", *Lab Chip*, 2005, 5, 1155-1160, The Royal Society of Chemistry 2005.

Chen et al., "Simultaneous detection of *Escherichia coli* O157:H7, *Salmonella* spp. and *Listeria monocytogenes* with an array-based immunosorbent assay using universal protein G-liposomal nanovesicles", *Talanta*, 69 (2006) 232-238, Science Direct, Elsevier B.V.

(Continued)

*Primary Examiner* — In Suk Bullock
*Assistant Examiner* — Timothy G Kingan
(74) *Attorney, Agent, or Firm* — Fay Sharpe LLP

(57) ABSTRACT

A microfluidic chip comprises a substrate and a channel or multiple channels in the substrate. Each channel includes a tortuous path section or multiple tortuous path sections. A receptor for the detection of an analyte can be immobilized in a tortuous path section, for example by adsorption. Different receptors can be immobilized in different tortuous path sections of each channel or in different channels for simultaneous detection of multiple analytes. The chip is especially useful for running immunoassays, particularly ELISA.

32 Claims, 18 Drawing Sheets

OTHER PUBLICATIONS

Du et al., "Parallel Detection and Quantification Using Nin Immunoassays in a Protein Microarray for Drug from Serum Samples", *Biomedical Microdevices*, 7:2, 143-146, 2005, Springer Science + Business Media, Inc., Netherlands.

Dunbar et al., "Quantitative, multiplexed detection of bacterial pathogens: DNA and protein applications of the Luminex LabMAP™ system", *Journal of Microbiological Methods*, 53 (2003) 245-252, Elsevier Science B.V.

Eteshola et al., "Development and characterization of an ELISA assay in PDMS microfluidic channels", *Sensors and Actuators B*, 72 (2001) 129-133, Elsevier Science B.V.

Kartalov et al., "High-throughput multi-antigen microfluidic fluorescence immunoassays", *BioTechniques*, 40:85-90 (Jan. 2006), vol. 40, No. 1 (2006).

Liew et al., "Validating a custom multiplex ELISA against individual commercial immunoassays using clinical samples", *BioTechniques*, 42:327-333 (Mar. 2007), vol. 42, No. 3, 2007.

Lopez et al., "Innovative tools for detection of plant pathogenic viruses and bacteria", *Int Microbiol* (2003) 6:233-343.

Mendoza et al., "High-Throughput Microarray-Based Enzyme-Linked Immunosorbent Assay (ELISA)", *Bio Techniques*, 27:778-788 (Oct. 1999), vol. 27, No. 4 (1999).

Moss et al., "Detection of *Cryptosporidium* Antibodies in Sera and Oral Fluids Using Multiplex Bead Assay", *J. Parasitol.*, 90(2), 2004, pp. 397-404, American Society of Parasitologists 2004.

Khan et al., "Simultaneous Serodetection of 10 Highly Prevalent Mouse Infectious Pathogens in a Single Reaction by Multiplex Analysis", *Clinical and Diagnostic Laboratory Immunology*, Apr. 2005, p. 513-519.

Micheli et al., "Electrochemical immunosensor array using a 96-well screen-printed microplate for aflatoxin $B_1$ detection", *Biosensors and Bioelectronics*, 22 (2007) 1434-1440, Elsevier.

Rowe-Taitt et al., "Simultaneous detection of six biohazardous agents using a planar waveguide array biosensor", *Biosensors and Bioelectronics*, 15 (2000) 579-589, Elsevier.

Sato et al., "Microchip-based enzyme-linked immunosorbent assay (microELISA) system with thermal lens detection", *Lab Chip*, 2004, 4, 570-575, The Royal Society of Chemistry.

Situma et al., "Merging microfluidics with microarray-based bioassays", *Biomolecular Engineering*, 23 (2006) 213-231, Elsevier B.V.

Kim et al., "Magnetic force-based multiplexed immunoassay using superparamagnetic nanoparticles in microfluidic channel", *Lab Chip*, 2005, 5, 657-664, The Royal Society of Chemistry.

Wolf et al., "Simultaneous detection of C-reactive protein and other cardiac markers in human plasma using micromosaic immunoassays and self-regulating microfluidic networks", *Biosensors and Bioelectronics*, 19 (2004) 1193-1202, Elsevier B.V.

Zaytseva, et al., "Development of a microfluidic biosensor module for pathogen detection", *Lab Chip*, 2005, 5, 805-811, The Royal Society of Chemistry.

Zhang et al., "An Anti *E. Coli* O157:H7 Antibody-Immobilized Microcantilever for the Detection of *Escherichia Coli (E. coli)*", *Analytical Sciences*, Apr. 2004, vol. 20, 585-587, The Japan Society for Analytical Chemistry.

Jani et al., "Multiplexed immunoassays by flow cytometry for diagnosis and surveillance of infectious diseases in resource-poor settings", *The Lancet*, Infectious Diseases, vol. 2, Apr. 2002, 243-250.

Kuller et al., "Development of whole-virus multiplex flow cytometric assay for antibody screening of a specific pathogen-free primate colony", *Diagnostic Microbiology and Infectious Disease*, 53 (2005) 185-193, Elsevier.

Lash et al., "Comparison of three multiplex cytokine analysis systems: Luminex, SearchLight™ and FAST Quant®", *Journal of Immunological Methods*, 309 (2006) 205-208, Elsevier B.V.

Mead et al., "Food-Related Illness and Death in the United States", *Emerging Infectious Diseases*, vol. 5, No. 5, Sep.-Oct. 1999, Centers for Disease Control and Prevention, Atlanta, GA.

Rao et al., "Comparison of Multiplexed Techniques for Detection of Bacterial and Viral Proteins", *Journal of Proteome Research*, 2004, 3, 736-742, American Chemical Society.

Ray et al., "Development, validation, and implementation of a multiplex immunoassay for the simultaneous determination of five cytokines in human serum", *Journal of Pharmaceutical and Biomedical Analysis*, 36 (2005) 1037-1044, Elsevier B.V.

Rowe et al., "Array Biosensor for Simultaneous Identification of Bacterial, Viral, and Protein Analytes", *Anal. Chem.*, 1999, 71, 3846-3852, American Chemical Society.

Philipp Angenendt, "Progress in protein and antibody microarray technology", *DDT*, vol. 10, No. 7, Apr. 2005, pp. 503-511, Elsevier Ltd.

Angenendt et al., "3D Protein Microarrays: Performing Multiplex Immunoassays on a Single Chip", *Anal. Chem.*, 2003, 75, 4368-4372, American Chemical Society.

Ayriss et al., "High-Throughput Screening of Single-Chain Antibodies Using Multiplexed Flow Cytometry", *Journal of Proteome Research*, 2007, 6, 1072-1082, American Chemical Society.

Bai et al., "Enzyme-Linked Immunosorbent Assay of *Escherichia coli* O157:H7 in Surface Enhanced Poly(Methyl Methacrylate) Microchannels", *Biotechnology and Bioengineering*, vol. 98, No. 2, Oct. 1, 2007, Wiley Periodicals, Inc.

Bernard et al., "Micromosaic Immunoassays", *Anal. Chem.*, 2001, 73, 8-12, American Chemical Society.

Cui et al., "Rapid sample preparation method for PCR-based detection of *Escherichia coli* O157:H7 in ground beef", *Journal of Applied Microbiology*, 2003, 95, 129-134, The Society for Applied Microbiology.

De Jager et al., "Improved multiplex immunoassay performance in human plasma and synovial fluid following removal of interfering heterophilic antibodies", *Journal of Immunological Methods*, 300 (2005) 124-135, Elsevier B.V.

Deisingh et al., "Strategies for the detection of *Escherichia coli* O157:h7 in foods", *Journal of Applied Microbiology*, 2004, 96, 419-429, The Society for Applied Microbiology.

MJ Fritzler, "Advances and applications of multiplexed diagnostic technologies in autoimmune diseases", *Lupus* (2006) 15, 422-427, Edward Arnold (Publishers) Ltd.

Huelseweh et al., "A simple and rapid protein array based method for the simultaneous detection of biowarfare agents", *Proteomics*, 2006, 6, 2972-2981, Wiley-VCH Verlag GmbH & Co. KGaA, Weinheim.

Sasakura et al., "Microarray techniques for more rapid protein quantification: Use of single spot multiplex analysis and a vibration reaction unit", *Analytica Chimica Acta*, 564 (2006) 53-58, Elsevier B.V.

Sato et al., "Integration of an Immunosorbent Assay System: Analysis of Secretory Human Immunoglobulin A on Polystyrene Beads in a Microchip", *Analytical Chemistry*, vol. 72, No. 6, Mar. 15, 2000, American Chemical Society.

Sato et al., "Determination of Carcinoembryonic Antigen in Human Sera by Integrated Bead-Bed Immunoasay in a Microchip for Cancer Diagnosis", *Anal. Chem.*, 2001, 73, 1213-1218, American Chemical Society.

Silzel et al., "Mass-sensing, multianalyte microarray immunoassay with imaging detection", *Clinical Chemistry*, 44:9 2036-2043 (1998), Beckman Coulter, Inc.

Song et al., "Miniature biochip system for detection of *Escherichia coli* O157:H7 based on antibody-immobilized capillary reactors and enzyme-linked immunosorbent assay", *Analytica Chimica Acta*, 507 (2004) 115-121, Elsevier B.V.

Urbanowska et al., "Protein microarray platform for the multiplex analysis of biomarkers in human sera", *Journal of Immunological Methods*, 316 (2006) 1-7, Elsevier B.V.

Woodbury et al., "Elevated HGF Levels in Sera from Breast Cancer Patients Detected Using a Protein Microarray ELISA", *Journal of Proteome Research*, 2002, 1, 233-237, American Chemical Society.

Wiese et al., "Simultaneous Multianalyte ELISA Performed on a Microarray Platform", *Clinical Chemistry*, 47:8 1451-1457 (2001), American Association for Clinical Chemistry.

\* cited by examiner

MICROFLUIDIC CHIPS FOR RAPID MULTIPLEX ELISA

BACKGROUND

The present disclosure relates generally to devices, such as microfluidic chips, which can provide high-throughput detection of target analytes in samples, especially biological samples, using various assays. The disclosure also relates to processes for making and using such devices.

Enzyme-Linked Immunosorbent Assay ("ELISA") is one of the most commonly used methods of various immunoassays. It has been widely used for detection and quantification of biological agents (mainly proteins and polypeptides) in the biotechnology industry, and is becoming increasingly important in clinical, food safety, and environmental applications. ELISA typically uses an enzymatic reaction to convert substrates into products having a detectable signal (e.g., fluorescence). Each enzyme in the conjugate can covert hundreds of substrates into products, thereby amplifying the detectable signal and enhancing the sensitivity of the assay.

In this regard, ELISA is a form of quantitative immunoassay based on the use of antibodies (or antigens) that are linked to an insoluble carrier surface. These antibodies (or antigens) are then used to capture the element antigen (or antibody) in the test solution. The antigen/antibody complex is then detected by measuring the activity of an appropriate enzyme that had previously been covalently attached to the antigen (or antibody).

The general principles and procedures used in typical ELISA are described here with reference to a 96-well microtiter plate:

(a) The first antibody (specific for the antigen to be assayed) is added to an ELISA plate. The first antibody is allowed to adsorb to the solid substrate surface. The excess antibody is removed from the plate after incubation.

(b) The wells are filled with blocking solution. The blocking solution provides proteins, which adsorb to all protein-binding sites and prevent subsequent nonspecific binding of antibody to the plate.

(c) The sample is added. If the sample contains the targeted antigen, it will bond to the adsorbed first antibody to form an antigen-antibody complex. After incubation, the plate is washed.

(d) The conjugate solution is added. The conjugate (the second antibody) is an appropriate enzyme-labeled ligand (usually an antibody), which will bond to the antigen. The conjugate solution is discarded and the plate is washed after incubation.

(e) The developing solution containing the substrate is added, which reacts with the enzyme in the conjugate. Each enzyme is able to convert hundreds of substrate into products to enhance the sensitivity of the assay. The products of the reaction emit fluorescence or change the color of the solution.

This process requires a series of mixing (reaction) and washing steps, which involves a tedious and laborious protocol. It often takes many hours to two days to perform one assay due to the long incubation times during each step. These long incubation times are mostly attributed to inefficient mass transport from the solution to the surface, whereas the immunoreaction itself is a rapid process. The antibodies and reagents used in ELISA are also expensive.

To overcome these drawbacks, industry is miniaturizing and automating ELISA by using 384- or even 1536-well plates and robots to carry out the liquid-handling work. However, the robotic machine is very expensive and not suitable for point-of-use in small diagnostic and testing laboratories.

A potential approach is to use microfabricated microfluidic ELISA devices with automatic and reliable (precise) liquid handling functions. Because of their microscale dimensions, the devices can enhance the reaction efficiency, simplify procedures, reduce assay time and sample or reagent consumption, and provide highly portable systems.

BRIEF DESCRIPTION

Disclosed herein, in various exemplary embodiments, are devices, such as microfluidic chips, which are especially suitable for use with ELISA microassays. These devices are useful for detecting the presence of one or more target analytes in one or more sample fluids. Methods and processes of making and using such devices are also disclosed.

In certain embodiments, the device comprises a substrate; and a channel in the substrate, the channel being defined by a flowpath between an inlet and an outlet, wherein the flowpath includes at least one tortuous path section. The device may be a microfluidic chip.

In additional embodiments, a receptor, such as an antibody or an antigen, which is complementary to an analyte being tested for, is included or immobilized in the tortuous path section of the flowpath. The microfluidic chip can be used to detect the presence of an analyte, such as a target analyte, in a sample solution.

The at least one tortuous path section may be configured in various shapes, patterns, or arrangements, such as a serpentine path, a circular path, or other special paths. Alternatively, in the at least one tortuous path section, the flowpath may move in a first direction one or more times and move in a second direction one or more times. The first and second directions may be from 15 degrees to 345 degrees apart, including about 180 degrees apart.

The at least one tortuous path section may have a length of at least 20 mm within an area of about 2.65 mm by 3 mm. The channel may have a volume of from about 180 nanoliters to about 600 nanoliters.

The flowpath of the channel may include a plurality of tortuous path sections. The chip may further comprise a cover, wherein the cover forms a portion of the channel.

The chip may have a plurality of channels. The inlet of each channel may be connected to a common loading channel. Each channel may have a plurality of tortuous path sections, each tortuous path section having a receptor, such as an antibody or antigen, immobilized on its surface. In some embodiments, each channel has a plurality of tortuous path sections, the tortuous path sections having locations and dimensions corresponding to the locations and dimensions of wells in a 384-well plate.

In further embodiments, an antibody for the detection of an antigen can be immobilized in the tortuous path section. The microfluidic chip can be used to detect the presence of that antigen in a sample solution. Alternatively, an antigen can be immobilized in the tortuous path section to detect the presence of antibodies to that antigen in a sample solution. Other receptors which can be used to detect other types of analytes can also be immobilized in the tortuous path section.

In other embodiments, a device for detecting the presence of an analyte in a sample fluid comprises a substrate; and a channel in the substrate, the channel comprising an inlet, an outlet, and a flowpath connecting the inlet and outlet, wherein the inlet and outlet together define a midplane; and a portion of the flowpath travels transversely across the midplane.

A portion of the flowpath may travel transversely across the midplane multiple times. A portion of the flowpath may travel substantially perpendicularly across the midplane. The flowpath might not travel continuously towards the outlet from the inlet.

In further embodiments, the portion of the flowpath that travels transversely across the midplane includes a receptor, such as an antibody or an antigen, that is complementary to an analyte being tested for. Preferably, the receptor is immobilized on the surface of the flowpath.

The substrate may be made from a material selected from the group consisting of poly(methyl methacrylate), polystyrene, poly(dimethylsiloxane), polyethylene terephthalate, polyethylene, polypropylene, polylactic acid, poly(D,L-lactide-co-glycolide), polycarbonate, cyclic olefin copolymers, silicon, and glass.

In still other embodiments, a device, such as a microfluidic chip, is provided for analysis of a target analyte in a sample fluid. The device comprises a substrate; and a plurality of channels in the substrate, each channel being defined by a flowpath between an inlet and an outlet, wherein the flowpath contains at least one serpentine path section. A receptor complementary to the target analyte, such as an antibody or an antigen, may be immobilized on the surface of the flowpath in the serpentine path section.

In further embodiments, a method of using a device to analyze a sample for an analyte comprises:
  providing a sample and a device, the device comprising a substrate and a channel in the substrate, the channel being defined by a flowpath between an inlet and an outlet, the flowpath including a tortuous path section;
  immobilizing a receptor complementary to the analyte in the tortuous path section; and
  flowing the sample through the channel to perform an enzyme-linked immunosorbent assay on the sample. Optionally, means for detecting the results of the ELISA assay are also present.

In still further embodiments, a method of using a device to analyze a sample for multiple analytes comprises:
  providing a sample and a device, the device comprising a substrate and a channel in the substrate, the channel being defined by a flowpath between an inlet and an outlet, the flowpath including a plurality of tortuous path sections;
  including a different receptor in each tortuous path section, each receptor being complementary to an analyte; and
  flowing the sample through the channel to perform an enzyme-linked immunosorbent assay on the sample. Optionally, means for detecting the results of the ELISA assay are also present.

In other embodiments, a method of using a device to analyze a sample for multiple analytes comprises:
  providing a sample and a device, the device comprising a substrate and a plurality of channels in the substrate, each channel being defined by a flowpath between an inlet and an outlet, the flowpath including at least one tortuous path section;
  including a different receptor in each tortuous path section, each receptor being complementary to an analyte; and
  flowing a portion of the sample through each channel to perform an enzyme-linked immunosorbent assay on the portion of the sample being flowed through the channel. Optionally, means for detecting the results of the ELISA assay are also present.

In other embodiments, a method of using a device to simultaneously analyze multiple samples for multiple analytes comprises:
  providing multiple samples and a device, the device comprising a substrate and a plurality of channels in the substrate, each channel being defined by a flowpath between an inlet and an outlet, the flowpath containing a plurality of tortuous path sections;
  immobilizing a receptor complementary to an analyte in each tortuous path section; and
  flowing a different sample through each channel to simultaneously perform an enzyme-linked immunosorbent assay on each sample. Optionally, means for detecting the results of the ELISA assay are also present.

These and other non-limiting aspects and/or objects of the development are more particularly disclosed below.

BRIEF DESCRIPTION OF THE DRAWINGS

The following is a brief description of the drawings, which are presented for the purposes of illustrating various embodiments of the development disclosed herein and not for the purposes of limiting the same.

DETAILED DESCRIPTION

Figure 1:
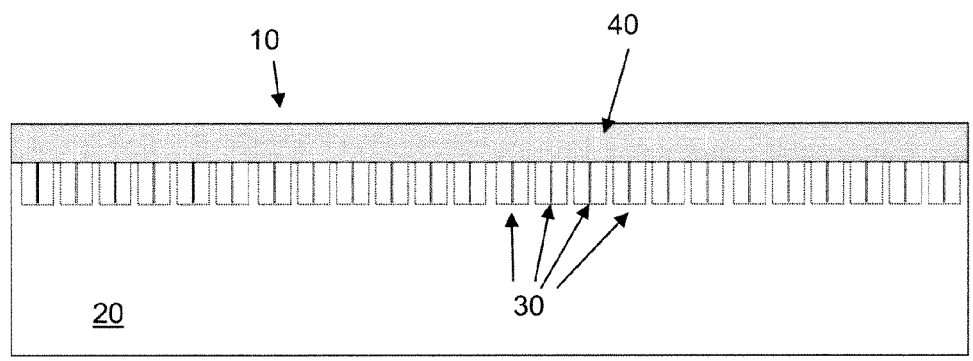
FIG. 1 is a side view of one embodiment of a device of the present disclosure.

A more complete understanding of the processes and apparatuses disclosed herein can be obtained by reference to the accompanying drawings. These Figures are merely schematic representations based on convenience and the ease of demonstrating the present development, and are, therefore, not intended to indicate relative size and dimensions of the instant devices or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to component of like function.

In an exemplary embodiment, the device comprises a substrate and a channel in the substrate, the channel being defined by a flowpath between an inlet and an outlet, wherein the flowpath includes at least one tortuous path section. The device may comprise a plurality of channels as well.

FIG. 1 is a cross-sectional view of an exemplary device. As depicted here, the device 10 is a microfluidic chip comprising a substrate 20 having multiple channels 30. As depicted here, there are a total of 24 channels. As shown here, the device 10 also comprises a cover 40 which forms a portion of each channel.

Figure 2:
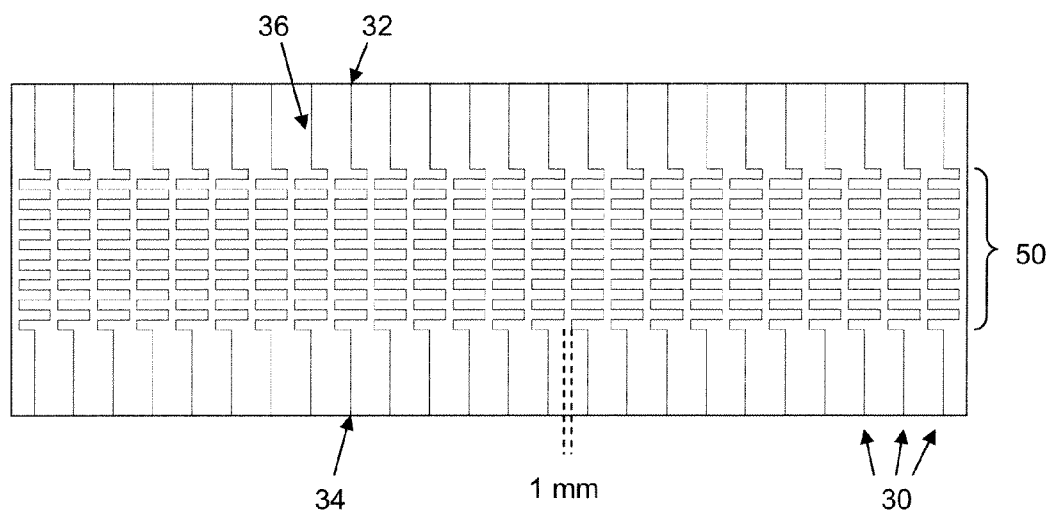
FIG. 2 is a top view of the one embodiment of a device of the present disclosure.

FIG. 2 is a top view of the same exemplary device. Each channel 30 comprises an inlet 32, an outlet 34, and a flowpath 36 between them, wherein the flowpath contains at least one tortuous path section 50.

Figure 3:
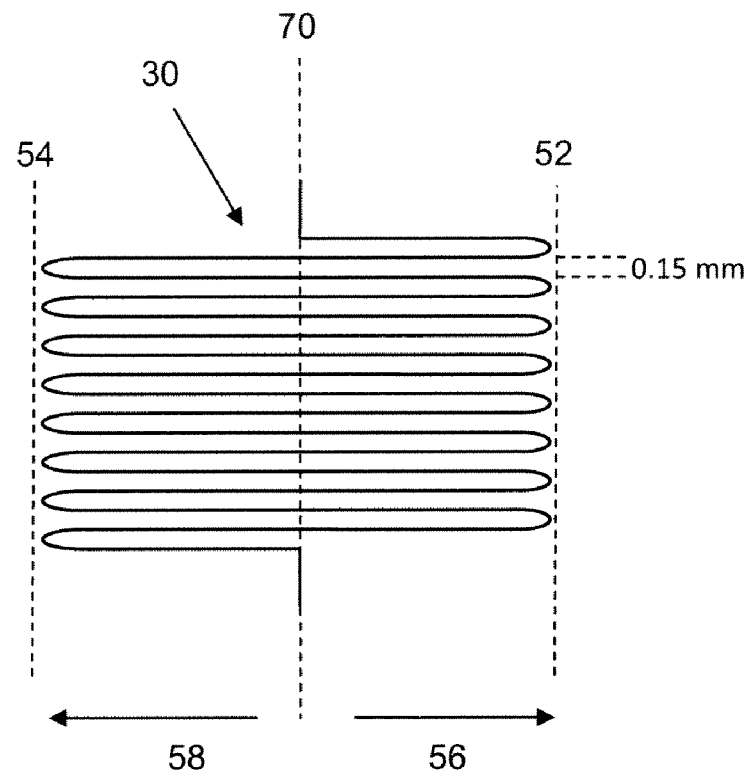
FIG. 3 is a top view of a tortuous path section having a serpentine path.

FIG. 3 is a top view of one embodiment of a channel 30. The tortuous path section 50 of this channel has the form of a serpentine path, in which the flowpath travels back and forth between a first side 52 and a second side 54. Alternately, the flowpath 36 may be described as moving back and forth from a first direction 56 to a second direction 58 one or more times. In the depicted embodiment, the first and second directions are about 180 degrees apart. However, this amount may vary; for example, they may be from about 15 degrees to about 345 degrees apart.

Figure 4:
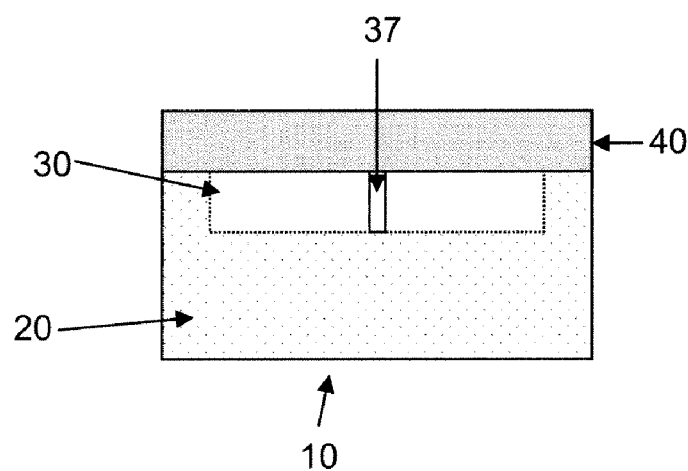
FIG. 4 is a side view of the tortuous path section having a serpentine path.

FIG. 4 is a side view of the same embodiment of the channel 30. As seen here, the cover 40 forms a portion of the channel 30. The channel has a rectangular cross-sectional shape 37. The channel has dimensions about approximately 0.1 mm width and 0.1 mm depth.

Referring back to FIG. 1, the depicted embodiment has a total channel length of about 56 mm. The gap between inter-channels is about 0.15 mm. The distance between adjacent channels is about 1 mm.

Figure 5:
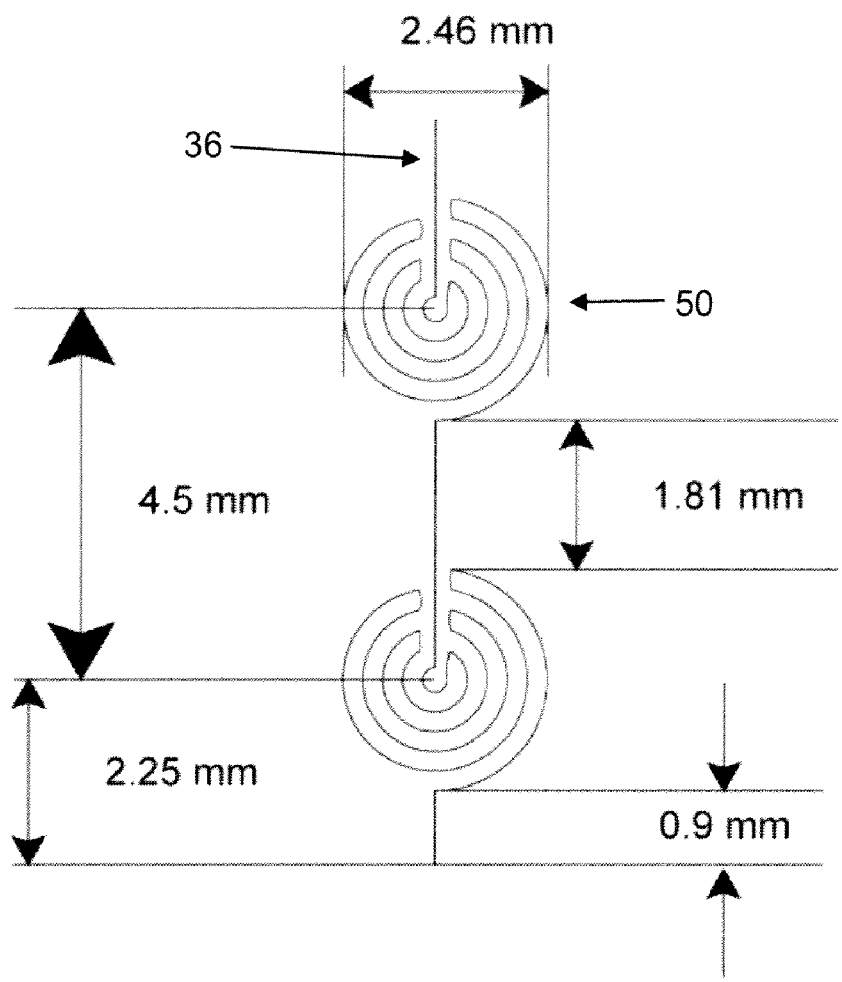
FIG. 5 is a top view of an embodiment of a channel having two circular path sections.
Figure 6:
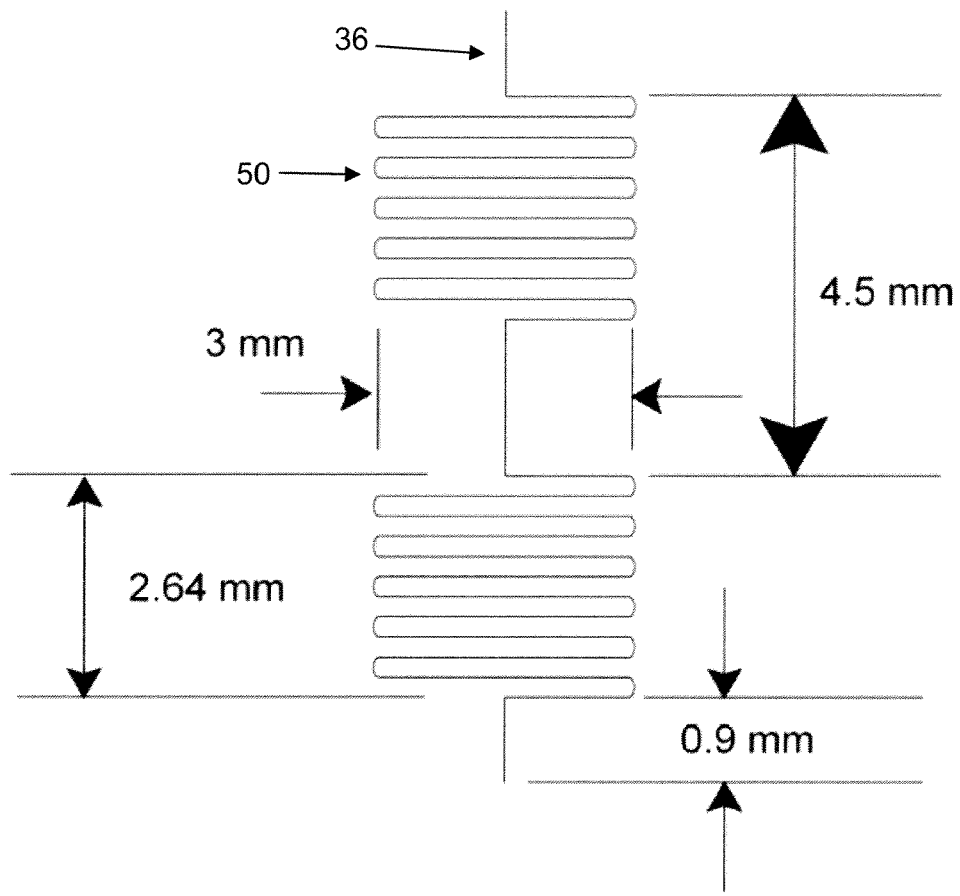
FIG. 6 is a top view of an embodiment of a channel having two serpentine path sections.

In other embodiments, the channel may have a plurality of tortuous path sections. FIG. 5 and FIG. 6 are top views of two embodiments of a channel having a plurality of tortuous path sections. The tortuous path sections 50 of FIG. 5 have the form of a circular path. In each tortuous path section, the flowpath 36 may be considered as continuously curving in a first direction and then continuously curving in a second direction. The tortuous path sections 50 of FIG. 6 have the form of a serpentine path.

As seen in FIG. 5, the circular path occurs in an area of about 2.5 mm by about 2.7 mm. As seen in FIG. 6, the serpentine path occurs in an area of about 2.7 mm by about 3.0 mm. The circular path has a length of about 21 mm and a volume of about 195 nanoliters (nL). The serpentine path has a length of about 56 mm and a volume of about 560 nL.

In embodiments, the tortuous path section provides a length of at least 20 mm within a rectangular area of about 2.5 mm by about 3.0 mm. In more specific embodiments, the length is at least 50 mm within the rectangular area. In other embodiments, the length is from about 20 mm to about 60 mm. In other embodiments, the tortuous path section has a volume of from about 180 nL to about 600 nL. This is much smaller than the volume of a microwell in a 384-well microtiter plate, which is typically about 30 to 50 microliters. In channels having multiple tortuous path sections, the tortuous path sections are generally separated by a distance long enough to prevent interference between sections based on diffusion.

The devices of the present disclosure may, in certain embodiments, also have a plurality of channels. In other embodiments, the channels may be laid out so that the tortuous path sections conform to the locations and dimensions of wells in, for example, a 384-well microtiter plate. Thus, existing microtiter plate readers can be used to read the results of an assay performed on the device.

Figure 7:
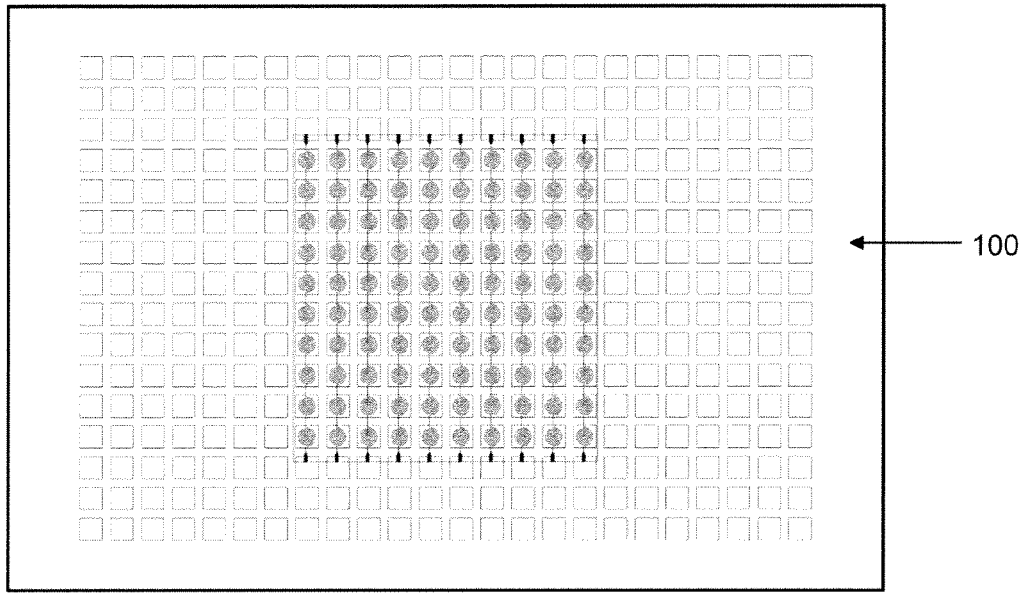
FIG. 7 is a top view depicting a device having 10 channels, each channel having 10 tortuous path sections.
Figure 8:
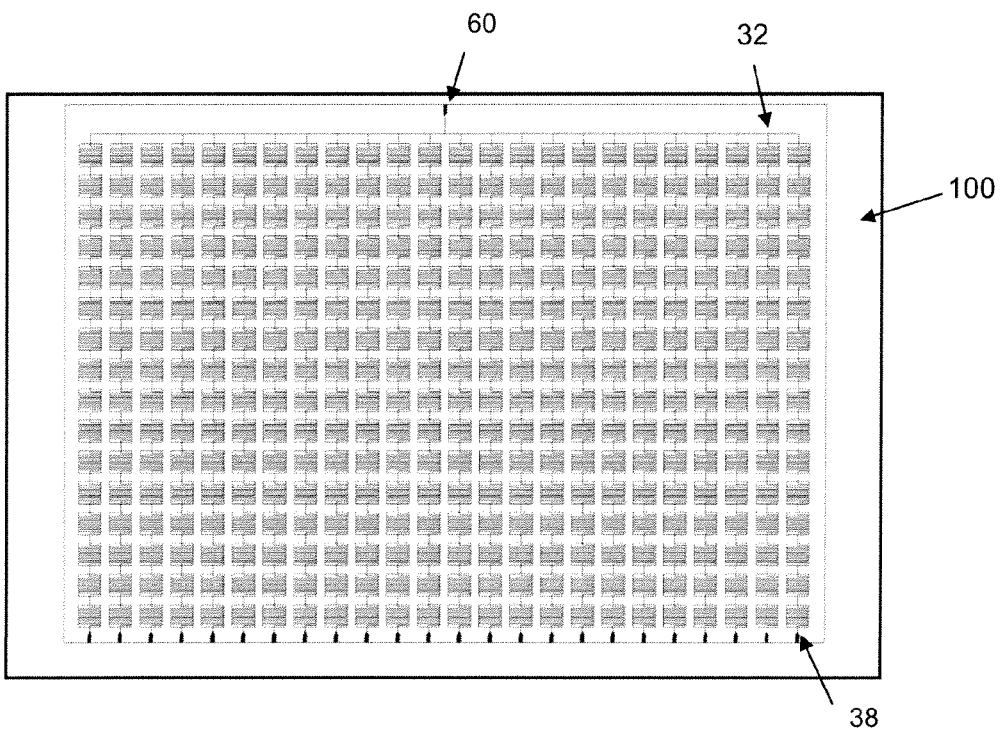
FIG. 8 is a top view depicting a device having 24 channels, each channel having 16 tortuous path sections.

FIG. 7 and FIG. 8 are top views of two embodiments of such a device. FIG. 7 is a top view depicting a device having 10 channels, each channel having 10 tortuous path sections. In this embodiment, the tortuous path sections are all circular paths. Each tortuous path section has a length of about 21 mm and a volume of about 195 nL. The gap between inter-channels is about 0.15 mm. The distance between adjacent channels is about 2 mm.

FIG. 8 is a top view depicting a device having 24 channels, each channel having 16 tortuous path sections. In this embodiment, the tortuous path sections are all serpentine paths. Each tortuous path section has a length of about 35 mm and a volume of about 317 nL. The device is depicted over a 384-well microtiter plate 100. In addition, FIG. 8 depicts a common loading channel 60 which is connected to the inlet 32 of each channel 30.

The tortuous path section allows the channel to provide a greater surface area to volume ratio than the normal well of a microtiter plate. Because immunoreaction time is based on diffusion, this greater ratio allows diffusion to occur more rapidly, reducing the time needed for the immunoassay to occur.

Figure 9:
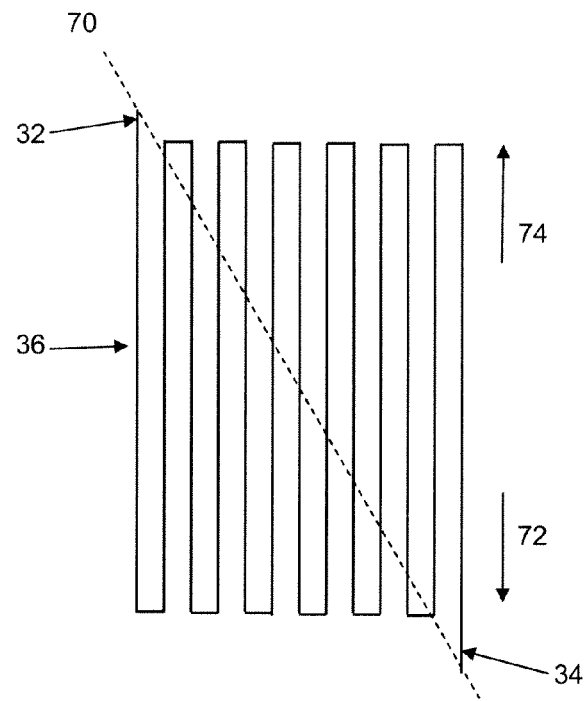
FIG. 9 is a third embodiment of a tortuous path section.
Figure 10:
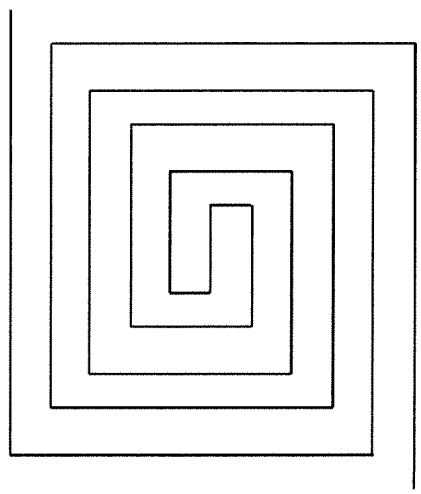
FIG. 10 is a fourth embodiment of a tortuous path section.
Figure 11:
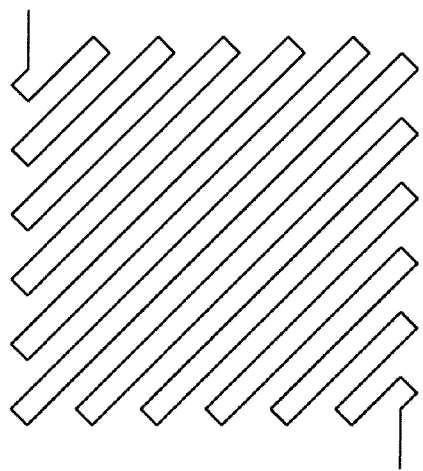
FIG. 11 is a fifth embodiment of a tortuous path section.

More generally, the tortuous path section of the channel may have any orientation and fit within an area having any dimensions. FIGS. 9-11 show three additional exemplary embodiments of tortuous path sections having various orientations. Again, each embodiment may fit within an area of about 2.5 mm by about 3.0 mm.

In embodiments where a channel has a plurality of tortuous path sections, the tortuous path sections may vary. For example, a channel may have two tortuous path sections, wherein one section is a serpentine path and the other section is a circular path. Similarly, in embodiments where the device has a plurality of channels which have a plurality of tortuous path sections, each of the tortuous path sections in each channel may vary. However, the tortuous path sections are generally all the same for ease of manufacturing.

In another exemplary embodiment, the device comprises a substrate and a channel in the substrate, the channel comprising an inlet, an outlet, and a flowpath connecting the inlet and outlet. The inlet and outlet can be considered as two points which together define a midplane. A portion of the flowpath travels transversely across the midplane.

For example, referring to FIG. 3, the inlet 32 and outlet 34 define a midplane 70. The flowpath 36 travels transversely across the midplane 70; here, the flowpath 36 travels transversely across the midplane 70 multiple times in both directions 56 and 58. In addition, the flowpath of FIG. 3 travels substantially perpendicularly across the midplane. FIG. 9 shows another example of the flowpath 36 traveling transversely across the midplane 70 multiple times. In FIG. 9, additionally, the flowpath does not travel continuously toward the outlet 34 from the inlet 32. Instead, the flowpath travels towards the outlet 34 when flowing in first direction 72. Put in other words, if the flowpath is seen as a vector using the midplane as one axis, the component of the vector that is parallel to the midplane moves towards the outlet. However, the flowpath travels towards the inlet 32 when flowing in second direction 74. Put another way, the component of the vector that is parallel to the midplane moves towards the inlet.

When the device does not contain a common loading channel, the channels can be loaded by directly dipping one end of the device into the reagent solution, which allows the solution to flow into the channels by capillary force. After a given incubation period, the reagents or solutions in the channels can be drained by a vacuum pump from the other end. This makes loading very simple. When a common loading channel is present, reagents can be simultaneously loaded into all channels by capillary force or a pressure difference imposed by using a syringe or vacuum pump. This replaces the use of multichannel pipettes.

The devices of the present disclosure can be used in several different ways. In devices having multiple channels, each channel can be used to analyze a different sample for multiple analytes. In such cases, referring to FIG. 8, the reagents common to each channel can be loaded through common loading channel 60 and the individual samples can be loaded through a separate input 38, unique to each channel, located on the other end of the device. Each channel contains multiple tortuous path sections and a receptor is placed in each tortuous path section of a particular channel. Generally, each channel on the device will test for the same analytes in each sample. A common sample can be analyzed for multiple analytes in at least two ways. Referring to FIGS. 5 and 6, receptors complementary to different analytes can be immobilized in a channel and the sample is then flowed through that channel. Here, the tortuous path sections may be considered to be in series. Alternatively, referring to FIG. 2, a device may have multiple channels. Receptors complementary to different analytes are immobilized in each tortuous path section and the sample is then flowed through a common loading channel and flowed through each of the channels. Here, the tortuous path sections may be considered to be in parallel. Optionally, the device may include a means for detecting and/or quantifying the results of the assay in the channel. Such means may include means for detecting a light signal, such as a photomultiplier tube, a camera, a plate reader, or other optical device. The methods may also include detecting the product of an enzyme-linked reaction in the tortuous path section(s) of the channel.

The devices of the present disclosure provide simple and accurate loading with precise reagent volume. Instead of the need to accurately measure liquid volumes by pipetting, a fixed amount of reagent is delivered into a fixed channel volume. Therefore, the results are not dependent on the accuracy of sample loading by pipetting, as with a multiwall plate. The devices also have many advantages, including faster time-to-result, reduced reagent usage, enhanced detection sensitivity, and better assay accuracy. The design of the tortuous path section provides greater surface area compared to a straight channel, allowing easier detection with an existing plate reader. In the last step of ELISA (reacting substrate with the enzyme conjugates on the second antibody) the resulting product is localized within the tortuous path section, allowing one channel with multiple tortuous path sections to operate like many microwells. This design allows multiplex analysis for multiple targets or multiple samples to be carried out on the same device.

The device can be made from polymers, such as PMMA, using soft photolithography and microembossing methods. Other exemplary substrates include polystyrene, poly(dimethylsiloxane), polyethylene terephthalate, polyethylene, polypropylene, polylactic acid, poly(D,L-lactide-co-glycolide), polycarbonate, cyclic olefin copolymers, silicon, and glass.

The device can be useful in several applications. It can enable rapid detection and characterization of food-borne pathogens and toxins, as well as water-borne materials, including allergens, pollutants, heavy metals, and antigens in biological samples such as blood and body fluids. It may also be used for screening to detect early-stage cancer, immunodiseases, or HIV.

The following examples are provided to illustrate the methods and apparatuses of the present disclosure. The examples are merely illustrative and are not intended to limit devices made in accordance with the disclosure to the materials, conditions, or process parameters set forth therein. All parts are percentages by weight unless otherwise indicated.

EXAMPLES

Example 1

Fabrication:

A microfluidic chip containing eight channels, each with three tortuous path sections, was fabricated using the following process. A photoresist mother mold (SU-8 100, Microchem) with the multichannel design was fabricated through a standard photolithographic process. Polydimethylsiloxane (PDMS) was prepared from Sylgard 184 silicon elastomer base and curing agent (Dow Corning Corporation, Midland, Mich.) at a 10:1 (w/w) ratio. After thorough mixing and degassing under vacuum for 30 min, the PDMS polymer was casted over the mother mold and cured in an oven at 70° C. for 1.5 to 2 hrs. The PDMS daughter mold was then used to produce poly(methyl methacrylate) (PMMA) multichannel chips through a hot micro-embossing process using a digitized hot press (Carver, Wabash, Ind.). Chips with circular or serpentine paths were fabricated.

The PMMA chips were functionalized with poly(ethyleneimine) (PEI; Mw 75,000, Sigma Chemicals, St. Louis, Mo.) to enhance surface binding of the first antibody. The PMMA chips were directly immersed in the PEI solution (0.2%, pH 11.5) at 25° C. for 1 hr. 0.1 N NaOH or 0.1 N HCl was used to adjust the pH value of the PEI solution. The functionalized PMMA chips were then placed in the glutaraldehyde (GA; Sigma Chemicals, St. Louis, Mo.) solution (1% w/v) at room temperature for 30 min. The PMMA surface was thoroughly rinsed with distilled water after each treatment step. Finally, the treated PMMA chips were air-dried and ready for antibody binding.

Reagent Preparation:

Heat-killed *Campylobacter jejune*, *Escherichia coil* O157:H7, *Salmonella typhimurium* cells (antigens), affinity purified polyclonal antibodies to *Campylobacter* cells, *E. coli* O157:H7, or *Salmonella* common structural antigens (CSA) made in goat (first antibodies), and affinity purified polyclonal antibodies to *Campylobacter* cells, *E. coli* O157:H7, or *Salmonella* CSA labeled with horseradish peroxidase (second antibody) purchased from Kirkegaard & Perry Laboratories, Inc. (Gaithersburg, Md.), were reconstituted in distilled water and stored at minus 80° C. until use. The substrate solution was prepared by dissolving 3 mg/mL of 3-(p-hydroxyphenyl)-propionic acid (HPPA) (Sigma Aldrich, St. Louis, Mo.) in Tris-HCl buffer (0.15 M, pH 8.5). Prior to use, 1 µL of 30% hydrogen peroxide (Sigma Aldrich, St. Louis, Mo.) was added to every 7.5 mL of HPPA solution and mixed thoroughly. The washing buffer (PBW) was prepared by adding 0.1% polyoxyethylene-20 sorbitan monolaurate (Tween 20; Bio-Rad Laboratories, Hercules, Calif.) and 0.02% bovine serum albumin (BSA; Invitrogen Corporation, Grand Island, N.Y.) to Dulbecco's phosphate buffered saline (PBS, pH 7; Invitrogen Corporation, Carlsbad, Calif.). The blocking solution contained 0.1% Tween 20, 1% BSA, and 0.05% sodium azide (Sigma Aldrich, St. Louis, Mo.) in PBS.

ELISA Assay:

ELISA on microfluidic chips of the present disclosure, 96-well microtiter plate, or 384-well microtiter plate (Floutrac 200; Greiner Bio-One, Inc., Longwood, Fla.) was carried out as described below unless otherwise noted.

For the assay on PEI-treated multichannel chips, each channel was loaded with 1.5 μL of the first antibody solution (10 μg/mL) and incubated for 20 min. After incubation, the microchip was washed, air-blow dried, sealed with Scotch tape, and the chip surface was treated with the blocking solution for 1 hr at 37° C. (or 20 hr at 4° C.). After blocking, 1.5 μL of the antigen mixture solution (mix two or three of antigen solutions of following concentrations: $1.6 \times 10^7$ cell/mL Campylobacter, $1 \times 10^7$ cell/mL E. coli O157:H7, $1.7 \times 10^7$ cell/mL Salmonella) was added into each channel and incubated for 1 hr (each antigen was applied to examine the detection limit using the concentration as follows: Campylobacter $0\text{-}4.8 \times 10^7$ cell/mL, E. coli O157:H7: $0\text{-}3 \times 10^8$ cell/mL, Salmonella: $0\text{-}5 \times 10^8$ cell/mL). Then, 1.5 μL of the second antibody (1 μg/mL) solution were added to form the conjugate in 20 min. The substrate solution (1.5 μL) was introduced for the enzymatic reaction right before the detection of fluorescent product. Incubation was done in a humidified box to prevent the evaporation of reagents. The channel was thoroughly washed with 1.5 μL of PBW solution for three times between each step. The Scotch tape was replaced with a new one prior to the enzymatic reaction to eliminate undesired binding of the antibody and antigen on the Scotch tape. Results are an average of 3 replicates.

For the optimization of antibody concentrations of Campylobacter, the same ELISA procedure was followed using various amounts of the first antibody (0.1, 1, 10, 100 μg/mL) and the second antibody (0.1, 1, 5, 10 μg/mL) with $4.8 \times 10^7$ cells/mL Campylobacter jejuni.

A mixture of the second antibodies (1 μg/mL of Campylobacter, E. coli O157:H7, and Salmonella) was introduced in the multichannels to study the cross-reactivity of the second antibodies. The results were compared with the multichannel ELISA applying each corresponding (pure) second antibody following the same ELISA procedure.

For ELISA in 96-well or 384-well microtiter plates, 100 μL (96-well plate) or 30 μL (384-well plate) of each of the following solutions were added to each well in sequence: first antibody (10 μg/mL), blocking (300 μL for 96-well plate and 90 μL for 384-well plate), mixture of antigens (same concentrations used on the multichannel ELISA; $0\text{-}5 \times 10^7$ cell/mL Salmonella for studies on the detection limit), second antibody (1 μg/mL), and substrate solutions. Between adding different solutions, the individual wells were washed with the PBW solution (200 μL for 96-well plate and 60 μL for 384-well plate) three times. The incubation steps were done at room temperature for 3 hr, except 4 hr incubation for antigen and the blocking for 3 hr at 25° C. (or 20 hr at 4° C.). All experiments were performed in triplicate.

The rate of fluorescence intensity of the enzymatic reaction product (relative fluorescence unit per second: RFU/s) was monitored as a function of time and used as an indicator of the amount of the conjugated antibody, which is usually proportional to the amount of the first antibody bound on the surface or amount of antigen captured in the assay. The signal-to-noise (S/N) ratio was estimated by the detected fluorescence intensity divided by the fluorescence intensity of background noise.

All detection (including 96-well, 384-well microplate, microchannel, and multichannel ELISAs) was measured using a TECAN GENios Pro multidetection microplate reader with the excitation filter and emission filter at 320 nm and 405 nm (20 nm bandpass), respectively. The microchips were attached on the designed plate holder to fit in the reader. The detection was carried out from the bottom reading of the fluorescence. X-Fluor software or Magellan "Data Reduction" reader software was used to record and analyze the fluorescence intensity.

Surface Blocking Test:

Some channels immobilized with the first antibody were treated with a blocking reagent (no blocking, 1% BSA, 0.1% Tween 20+1% BSA, 1% Tween 20, and 1% Prionex® (Centerchem, Norwalk, Conn.)) to evaluate their efficacy of preventing nonspecific protein binding. The same ELISA procedure was followed with $5 \times 10^7$ cell/mL Salmonella. The background noise was used to indirectly assess the amount of antigen (Salmonella) and second antibody nonspecific bound to the surface, which indicated the capacity of the different blocking conditions.

Effect of Substrate Concentration on ELISA:

The effect of the amount of substrate solution on ELISA performance was studied to optimize their concentrations for Salmonella detection on the multichannel chips. The same ELISA procedure was followed using substrate solution with various amount of HPPA (6.02, 12.04, 18.05, 24.07, 30.09, 36.11 mM) or hydrogen peroxide (0.12, 0.23, 0.59, 1.17, 2.93, 5.87, 8.80, 11.73 mM) with $5 \times 10^7$ cells/mL Salmonella.

Results:

The results for the detection of multiple foodborne bacteria in a 96-well microtiter plate are shown in Table 1. They are reported as fluorescence signal and background noise (control) in unit of RFU/s.

TABLE 1

| Antibody | Antigen | | | | | | | |
| --- | --- | --- | --- | --- | --- | --- | --- | --- |
| | C* | E | S | C, E | C, S | E, S | C, E, S | Control |
| C | 5.96 ± 0.39 | 3.60 ± 0.58 | 2.14 ± 0.03 | 5.49 ± 0.49 | 5.38 ± 0.28 | 2.79 ± 0.39 | 5.54 ± 0.12 | 2.42 ± 0.45 |
| E | 0.90 ± 0.08 | 43.63 ± 3.69 | 0.78 ± 0.02 | 43.76 ± 4.21 | 1.02 ± 0.07 | 40.03 ± 1.60 | 40.32 ± 2.16 | 1.40 ± 0.53 |
| S | 3.73 ± 0.40 | 3.87 ± 0.25 | 28.46 ± 1.63 | 3.39 ± 0.17 | 27.62 ± 1.29 | 26.40 ± 1.35 | 23.10 ± 1.90 | 2.72 ± 1.00 |

Abbreviations:
C: Campylobacter jejuni,
E: E. coli O157:H7,
S: Salmonella typhimurium.
Control: no antigen in the sample.

The results for the detection of multiple foodborne bacteria in a 384-well microtiter plate are shown in Table 2.

TABLE 2

| Antibody | Antigen |  |  |  |  |  |  |  |
|---|---|---|---|---|---|---|---|---|
|  | C* | E | S | C, E | C, S | E, S | C, E, S | Control |
| C | 2.60 ± 0.10 | 1.34 ± 0.09 | 0.92 ± 0.09 | 2.22 ± 0.58 | 2.44 ± 0.44 | 1.36 ± 0.28 | 2.83 ± 0.05 | 1.91 ± 0.14 |
| E | 4.00 ± 0.89 | 14.92 ± 3.97 | 7.25 ± 1.59 | 19.48 ± 1.55 | 7.04 ± 0.43 | 19.73 ± 2.78 | 18.81 ± 0.77 | 5.32 ± 0.88 |
| S | 1.05 ± 0.19 | 0.86 ± 0.17 | 13.18 ± 3.57 | 1.73 ± 0.13 | 9.77 ± 2.29 | 10.68 ± 2.03 | 10.92 ± 0.84 | 0.83 ± 0.21 |

Abbreviations:
C: *Campylobacter jejuni*,
E: *E. coli* O157:H7,
S: *Salmonella typhimurium*.
Control: no antigen in the sample.

The results for the detection of multiple foodborne bacteria in a multichannel chip are shown in Table 3.

TABLE 3

| Antibody | Antigen |  |  |  |  |  |  |  |
|---|---|---|---|---|---|---|---|---|
|  | C* | E | S | C, E | C, S | E, S | C, E, S | Control |
| C | 6.78 ± 0.02 | 7.61 ± 0.19 | 6.13 ± 0.07 | 6.67 ± 0.32 | 5.41 ± 0.23 | 6.03 ± 0.12 | 6.59 ± 0.60 | 7.46 ± 0.19 |
| E | 2.70 ± 0.24 | 21.27 ± 3.21 | 2.78 ± 0.27 | 22.53 ± 3.14 | 2.16 ± 0.76 | 21.54 ± 0.79 | 21.78 ± 1.54 | 2.95 ± 0.40 |
| S | 3.87 ± 2.08 | 3.64 ± 1.10 | 15.20 ± 2.24 | 1.61 ± 0.31 | 13.06 ± 2.02 | 14.31 ± 3.69 | 12.11 ± 2.55 | 4.69 ± 1.00 |

Abbreviations:
C: *Campylobacter jejuni*,
E: *E. coli* O157:H7,
S: *Salmonella typhimurium*.
Control: no antigen in the sample.

In all three platforms, compared to the control, relatively high fluorescence signals were obtained at the wells where the loaded sample solution contained the antigen corresponding to the immobilized first antibody. The signals were comparable to the background noises if the sample solution was loaded to the wells in which no antigen corresponding to the first antibody was applied. This shows that each antigen (Campylobacter, *E. coli* O157:H7, or Salmonella) can specifically bind to the corresponding antibody.

Figure 12:
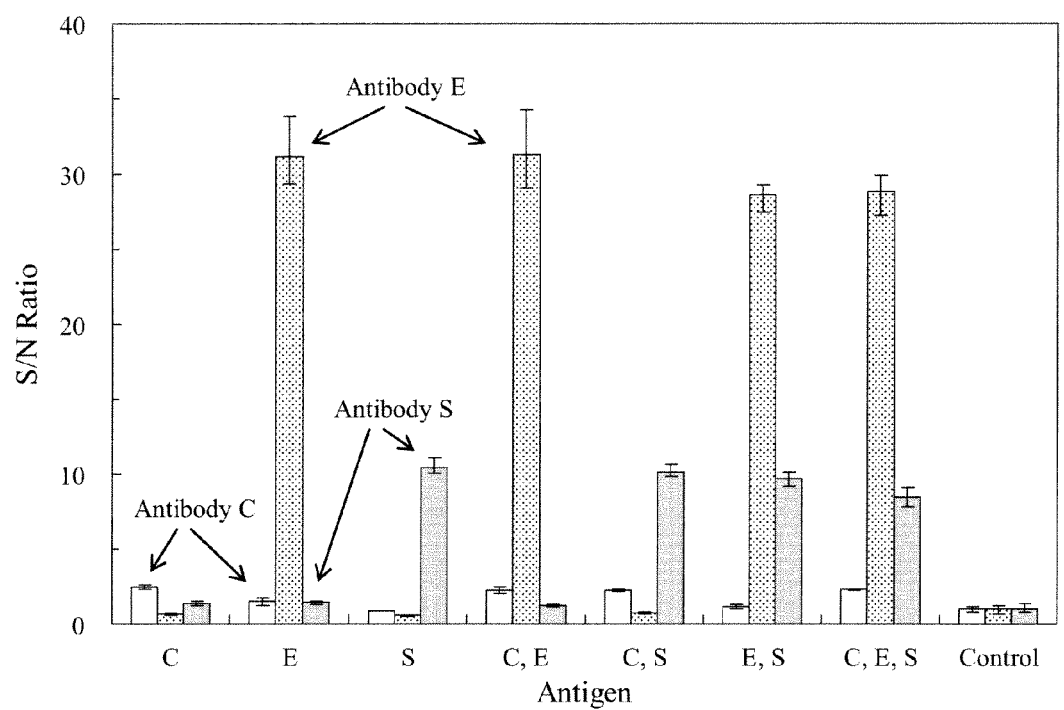
FIG. 12 is a graph showing the S/N ratio of various pathogens on a 96-well plate.
Figure 13:
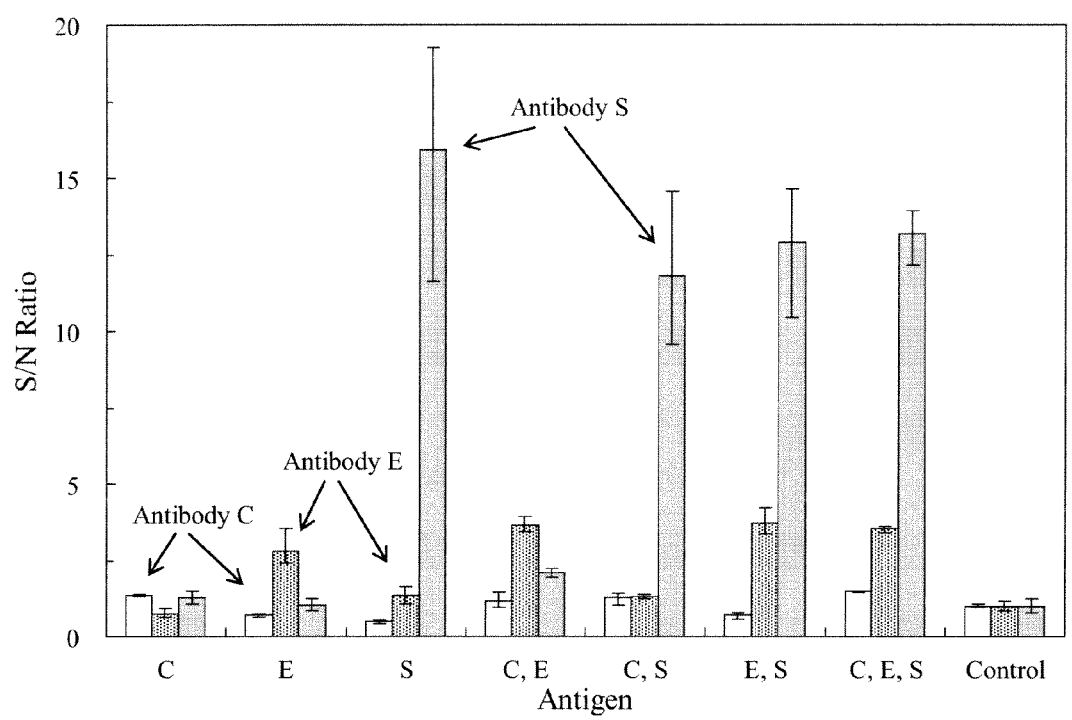
FIG. 13 is a graph showing the S/N ratio of various pathogens on a 384-well plate.
Figure 14:
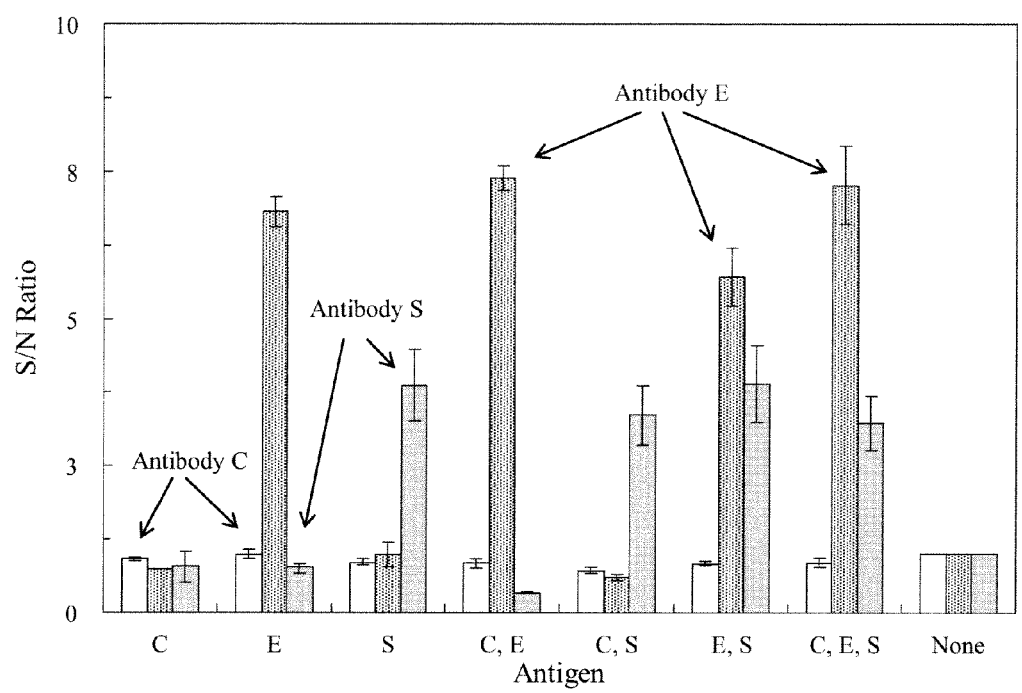
FIG. 14 is a graph showing the S/N ratio of various pathogens on a device of the present disclosure.

The S/N ratios for the 96-well plate, 384-well plate, and multichannel chip are shown in FIGS. 12-14, respectively. The S/N ratios for the detection of Campylobacter were not significant (less than 2.2~2.5) for any of the three platforms because of the relatively high background noise for this assay. In general, an S/N value of greater than 1.5 is needed to give a positive detection. However, *E. coli* O157:H7, Salmonella and their mixtures are successfully detected and are distinguishable from each other on the multichannel chip. Indeed, as can be seen in FIG. 14, higher S/N ratios were reached for the detection of *E. coli* O157:H7 on the multichannel chip FIG. 14) than in a 384-well microtiter plate (FIG. 13). It is noted, however, that as long as the S/N ratio is higher than 1.5, a positive detection can be confirmed.

Figure 15:
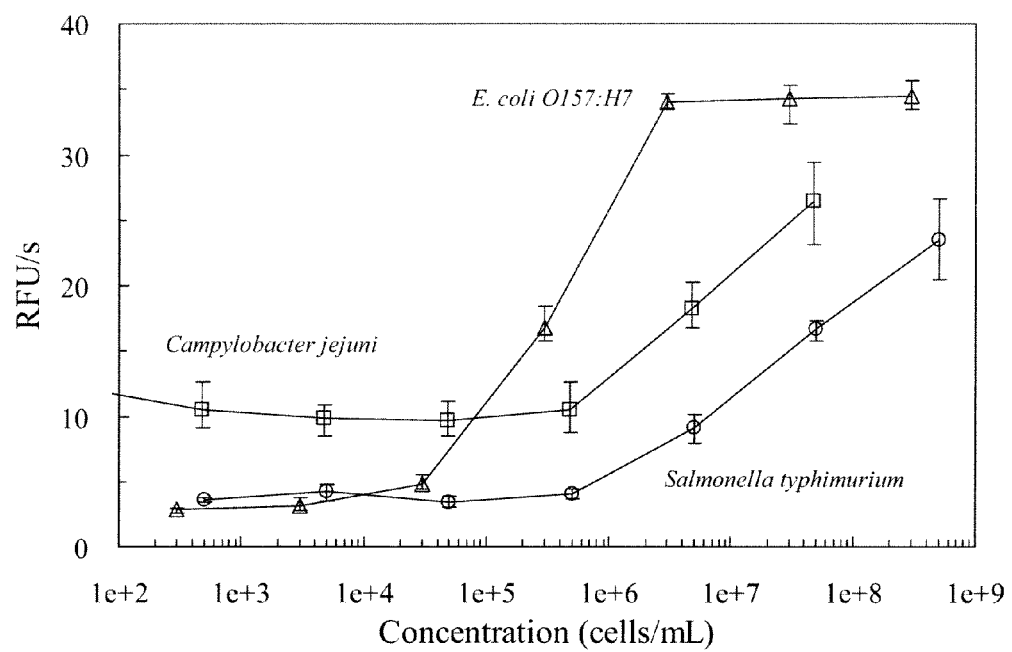
FIG. 15 is a graph of RFU/s versus cell concentration for a device of the present disclosure.
Figure 16:
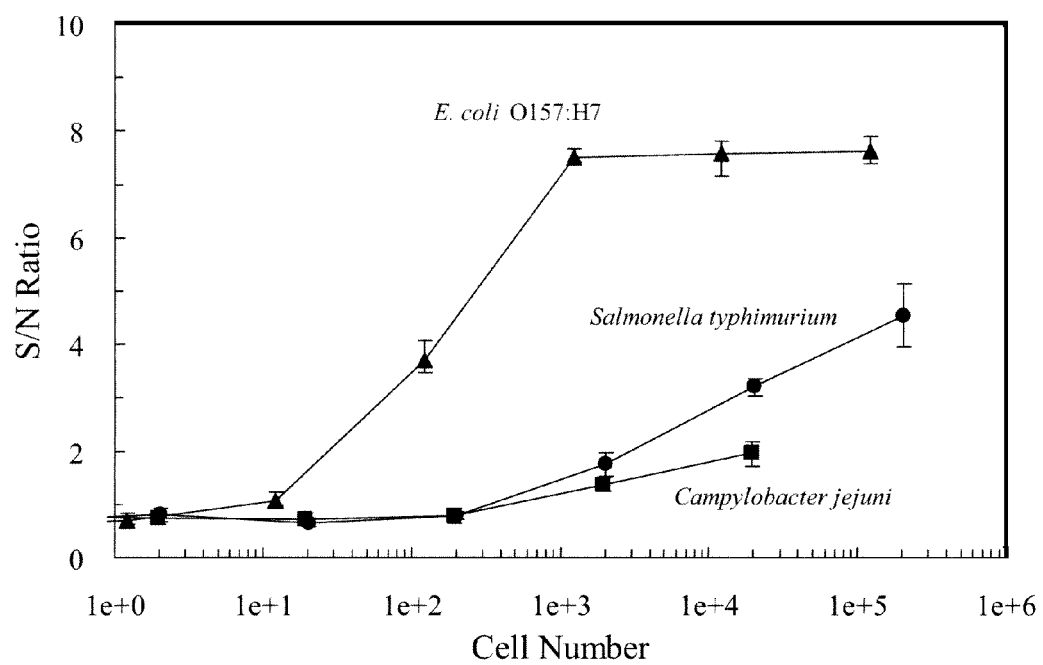
FIG. 16 is a graph of S/N ratio versus cell concentration for a device of the present disclosure.

Detection Limit of Multichannel ELISA:

The ELISA detection limits for the quantification of foodborne bacteria were performed on the multichannel chips. As shown in FIG. 15, the detection limits of the multichannel ELISA were estimated as $\sim3\times10^6$-$\sim4.8\times10^6$, $\sim3\times10^4$, and $\sim5\times10^5$ cells/mL for Campylobacter, *E. coli* O157:H7, and Salmonella, respectively. They were estimated by selecting the point where the RFU/s increased significantly. Conventional ELISA techniques usually have a detection limit of $10^5$-$10^6$ cfu/mL. As shown in FIG. 16, the detectable cell numbers on the multichannel chips are approximated to $1.9\times10^3$, 12, and 200 cells for Campylobacter, *E. coli* O157:H7, and Salmonella, respectively. They were estimated by selecting the point where the S/N ratio increased significantly.

Figure 17:
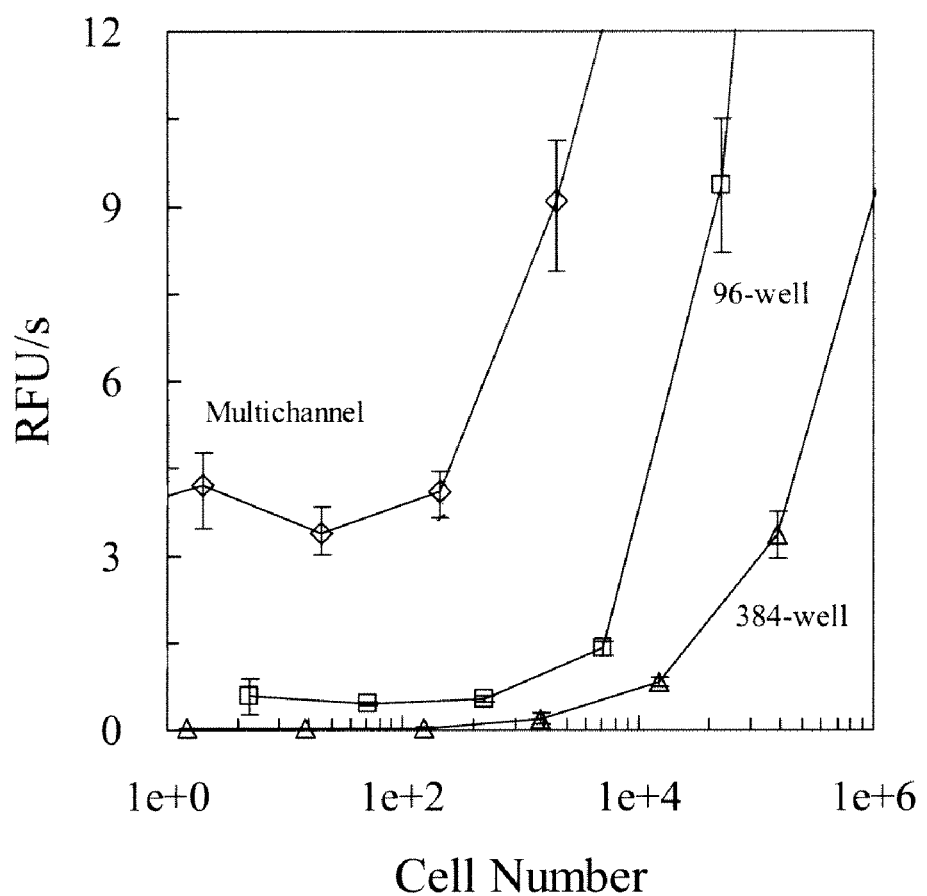
FIG. 17 is a graph of RFU/s versus cell number of *Salmonella typhimurium* for a 96-well plate, a 384-well plate, and a device of the present disclosure.
Figure 18:
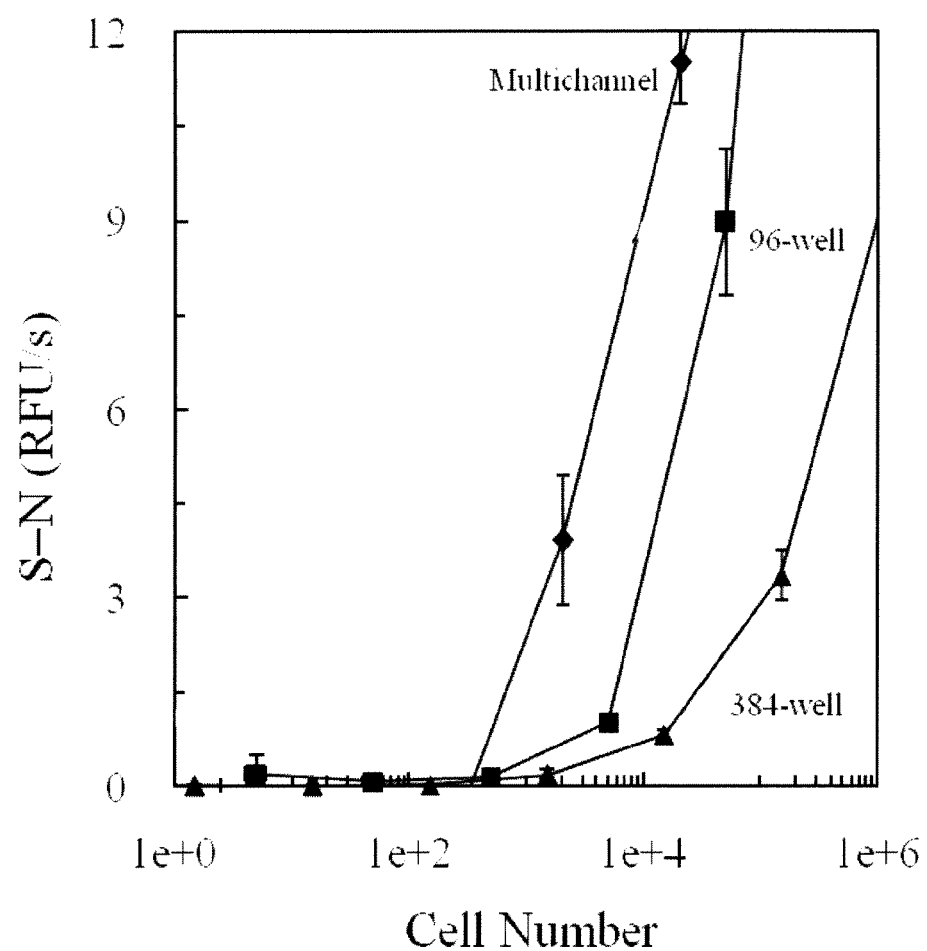
FIG. 18 is a graph of (Signal minus Noise) versus cell number of *Salmonella typhimurium* for a 96-well plate, a 384-well plate, and a device of the present disclosure.

FIG. 17 shows the signal versus cell number for the three platforms. FIG. 18 shows the (Signal minus Noise) versus cell number for the three platforms. Both are for the detection of *Salmonella typhimurium*. The multichannel ELISA is 1 to 2 orders more sensitive than the ELISA performed on the 384-well or 96-well microtiter plates as shown in FIGS. 17 and 18. The multichannel ELISA also had more precise S/N ratio (i.e. smaller error range) than the 384-well and 96-well microtiter plates.

Figure 19:
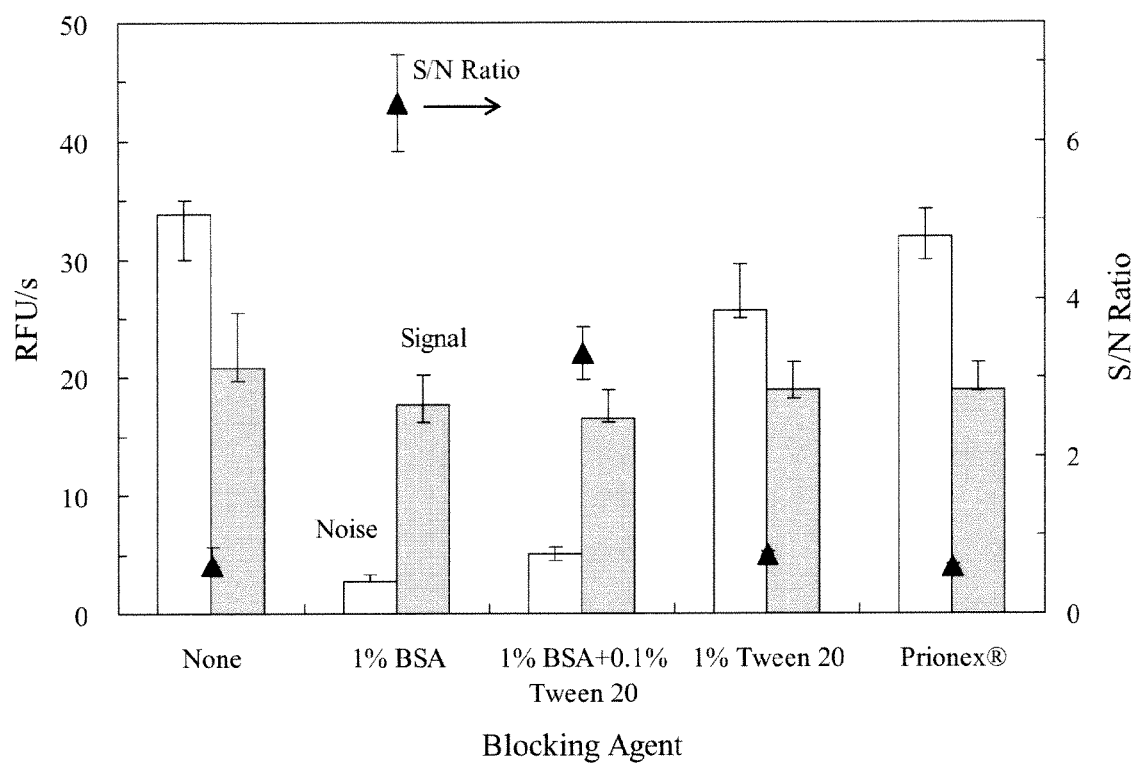
FIG. 19 is a graph showing the effective of various blocking agents in increasing the S/N ratio on a device of the present disclosure.

The multichannel ELISA greatly increased both the fluorescence signal and the background noise, but could diminish the S/N ratio. Therefore, it was of interest to optimize the blocking agents for the PEI-treated multichannel surface. A couple of protein solutions (BSA, Prionex®) and a surfactant (Tween 20) were used to reduce the nonspecific binding of antigen (Salmonella) or second antibody. As shown in FIG. 19, 1% Tween 20 solution and 1% Prionex® were not effective in blocking the surface, whereas 1% BSA solution was the most effective blocking agent examined; besides, the BSA solution enhanced the S/N ratio to 6.5 on the multichannel ELISA. Adding 0.1% Tween 20 to 1% BSA solution did not help reduce the nonspecific adsorption of proteins on the chip surface. Although BSA blocking sacrificed the signal intensity by 15% (compared to the surface without blocking), it apparently decreased 92% of the background noise as a result of the reduction of protein nonspecific binding and thus assured a more reliable assay with improved S/N ratio.

Figure 20:
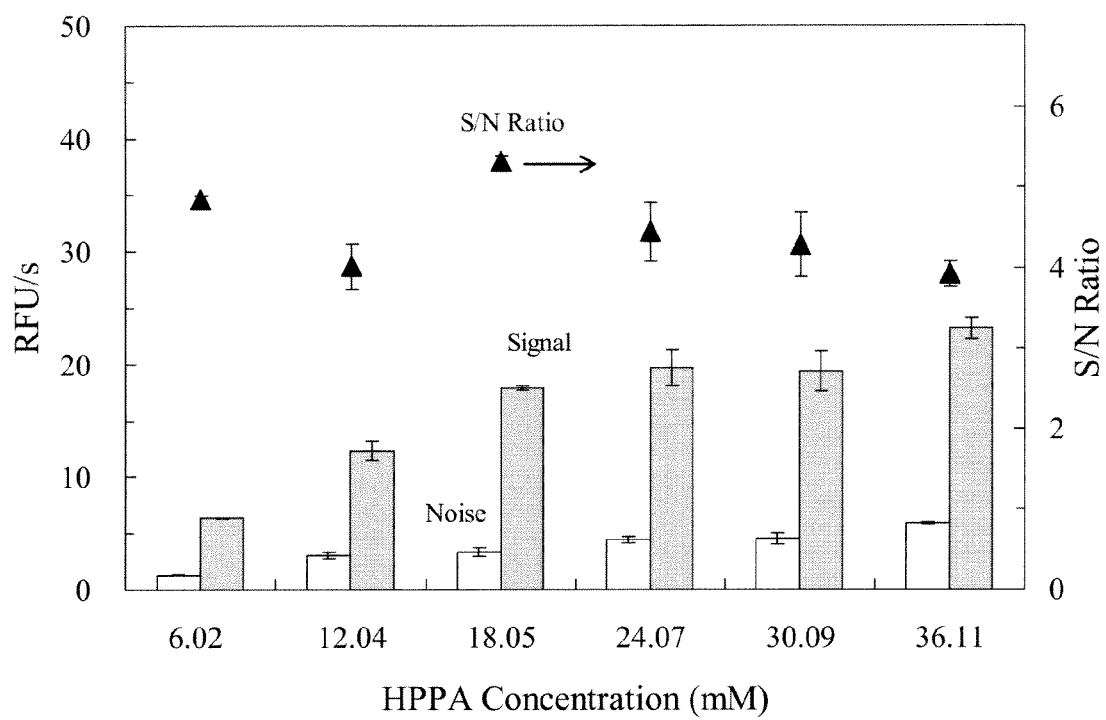
FIG. 20 is a graph showing the effect of HPPA concentration on S/N ratio.
Figure 21:
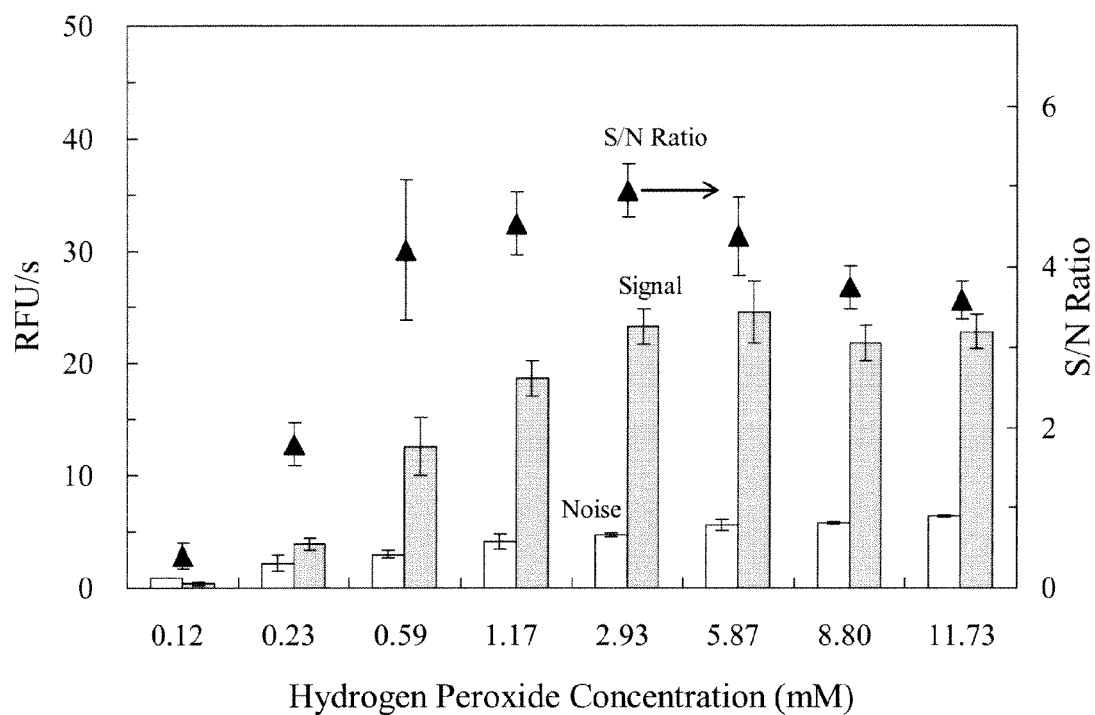
FIG. 21 is a graph showing the effect of $H_2O_2$ concentration on S/N ratio.

Effect of Substrate Concentration on ELISA:

To further improve the assay performance on the multichannel chip, the effects of the concentration of substrate (HPPA) and hydrogen peroxide ($H_2O_2$) were investigated. FIG. 20 shows that the background noise and fluorescence signal both gradually increased with increasing HPPA concentration when 1.17 mM $H_2O_2$ was added. The S/N ratios were almost the same with a maximum of 5.3 as the HPPA solution of 18.05 mM was applied. Accordingly, 18.05 mM HPPA was used for the optimization of $H_2O_2$ concentration (see FIG. 21). Similarly, the background noise gradually increased with increasing $H_2O_2$ concentration, but a plateau of the signal was attained and the S/N ratio reached the upper limit (~5.0) when 2.93 mM $H_2O_2$ was employed. Furthermore, there was little improvement in the S/N ratio when hydrogen peroxide concentration over 1.17 mM was added.

Figure 22:
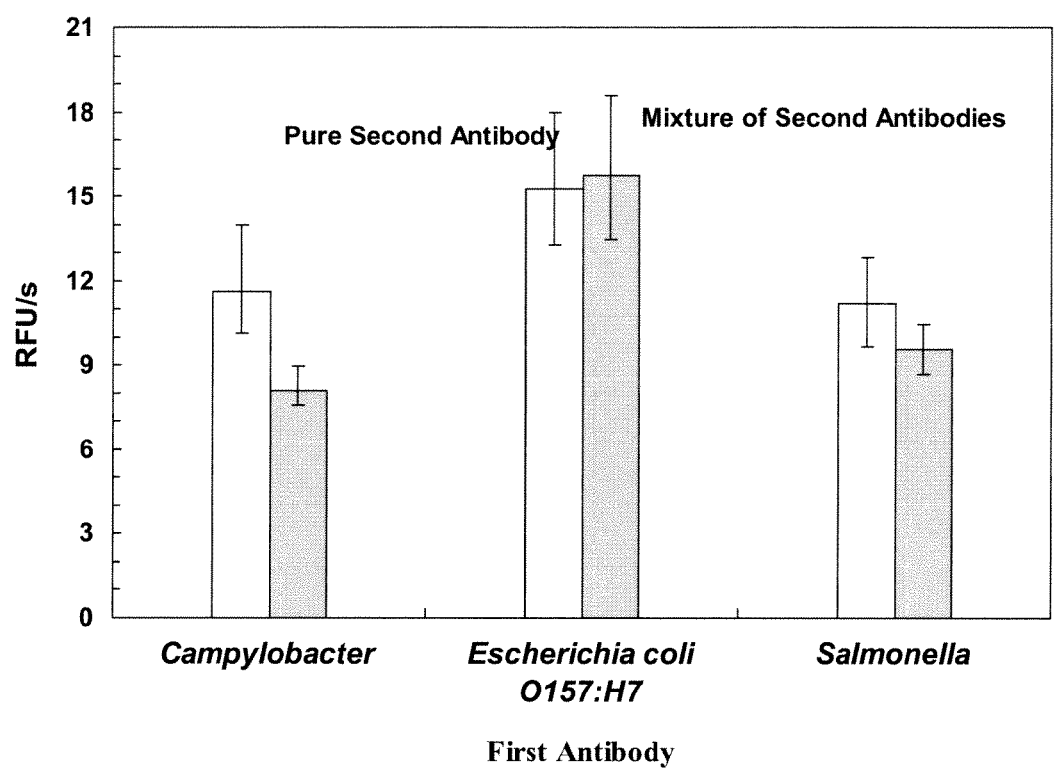
FIG. 22 is a graph showing the effect of antibody cross-reactivity on the obtained signal.

Cross-Reactivity of Second Antibody on Signal:

Antibody cross-reactivity is one problem in the practical application of ELISA. The mixture of second antibodies (*Campylobacter*, *E. coli* O157:H7, and *Salmonella*) was employed to examine the cross-reactivity of the second antibodies. The signals obtained from the detection of *E. coli* O157:H7 were comparable adding either pure second antibody or the mixture of second antibodies (see FIG. 22). However, compared to using only pure second antibody, the signal was decreased by 15-30% when a mixture of second antibodies was applied during the detection of *Campylobacter* or *Salmonella*. This may result from the cross-reaction of second antibodies or some unknown interference of the antigen-antibody conjugation among different species of bacteria. Nevertheless, the slightly reduced fluorescence signal would not affect the detection of these pathogens. Adding the mixture of the second antibodies together makes reagent loading easier and reduces labor in using the multichannel chip.

Example 2

Figure 23:
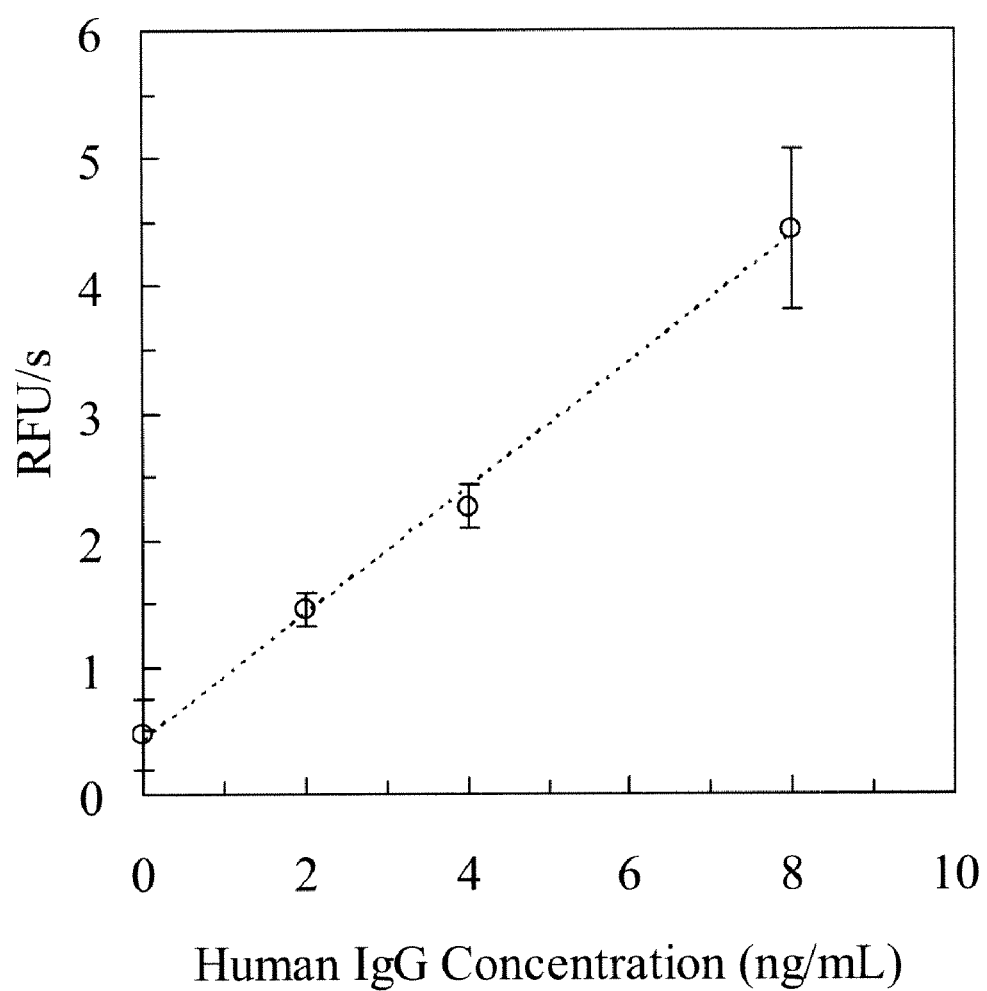
FIG. 23 is a graph showing the linearity of signal with concentration for human IgG in a device of the present disclosure.

Human IgG was used to calibrate a multichannel chip. Known concentrations of 0, 2, 4, and 8 ng/mL were applied and the resulting fluorescence was measured. The results are shown in FIG. 23. A linear response was obtained. The results were highly reproducible and the assay could be completed in less than one hour.

For comparison, Table 4 compares the multichannel chip with a 384-well plate. The four washing steps (one between each step) are ignored. The multichannel chip takes less time and uses less material (reagent).

TABLE 4

| | 384-Well Plate | | Multichannel Chip | |
|---|---|---|---|---|
| Step | Amount (µL) | Incubation Time (min) | Amount (µL) | Incubation Time (min) |
| 1st Antibody | 25 | >120 | 0.56 | <10 |
| Blocking | 25 | >120 | 0.56 | <10 |
| Sample | 25 | >120 | 0.56 | <10 |
| 2nd Antibody | 25 | >120 | 0.56 | <10 |
| Substrate | 25 | >5 | 0.56 | <1 |
| Total | 125 | >485 | 2.8 | <41 |

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

What is claimed is:

1. A microfluidic chip for detecting the presence of analytes in a sample fluid, comprising:
   a substrate; and
   a continuous channel in the substrate, the continuous channel being defined by a flowpath between an inlet and an outlet, the channel having a plurality of tortuous path sections, each tortuous path section having a different receptor immobilized on its surface, each receptor being complementary to one analyte being tested for.

2. The chip of claim 1, wherein each tortuous path section is a serpentine path.

3. The chip of claim 1, wherein each tortuous path section is a circular path.

4. The chip of claim 1, wherein in each tortuous path section, the flowpath moves in a first direction at least once and moves in a second direction at least once.

5. The chip of claim 4, wherein the first and second directions are from 15 to 345 degrees apart.

6. The chip of claim 4, wherein the first and second directions are about 180 degrees apart.

7. The chip of claim 1, wherein each tortuous path section has a length of at least 20 mm within an area of about 2.65 mm by 3 mm.

8. The chip of claim 1, wherein the channel has a volume of from about 180 nanoliters to about 600 nanoliters.

9. The chip of claim 1, further comprising a cover, wherein the cover forms a portion of the channel.

10. The chip of claim 1, wherein the chip has a plurality of continuous channels.

11. The chip of claim 10, wherein the inlet of each continuous channel is connected to a common loading channel.

12. The chip of claim 1, wherein the tortuous path sections have locations and dimensions corresponding to the locations and dimensions of wells in a 384-well plate.

13. The chip of claim 1, wherein each receptor is an antibody or antigen.

14. The chip of claim 1, wherein adjacent tortuous path sections in each continuous channel are separated by a path segment, the path segment having a length sufficient to prevent mixing between the adjacent tortuous path sections.

15. The chip of claim 14, wherein the length of each path segment is about 1.8 mm.

16. A device for detecting the presence of an analyte in a sample fluid, comprising:
   a substrate;
   and a continuous channel in the substrate, the continuous channel comprising an inlet, an outlet, and a flowpath connecting the inlet and outlet, wherein the inlet and outlet together define a midplane; and
   wherein the channel has a plurality of tortuous path sections, each tortuous path section having a different receptor immobilized on its surface, each receptor being complementary to an analyte being tested for:
   wherein in each tortuous path section, a portion of the flowpath travels transversely across the midplane.

17. The device of claim 16, wherein in each tortuous path section, the portion of the flowpath travels transversely across the midplane multiple times.

18. The device of claim 16, wherein in each tortuous path section, the portion of the flowpath travels substantially perpendicularly across the midplane.

19. The device of claim 16, wherein the flowpath does not travel continuously towards the outlet from the inlet.

20. The device of claim 16, wherein each receptor is an antibody or antigen.

21. The device of claim 16, wherein the device has a plurality of continuous channels.

22. The device of claim 21, wherein the inlet of each continuous channel is connected to a common loading channel.

23. The device of claim 16, wherein the substrate is made from a material selected from the group consisting of poly (methyl methacrylate), polystyrene, poly(dimethylsiloxane), polyethylene terephthalate, polyethylene, polypropylene, polylactic acid, poly(D,L-lactide-co-glycolide), polycarbonate, cyclic olefin copolymers, silicon, and glass.

24. The device of claim 16, further comprising a detector for detecting the product of an enzyme-linked reaction.

25. A method of using a microfluidic chip to analyze a sample for an analyte, comprising:
providing a sample and a microfluidic chip, the chip comprising a substrate and a continuous channel in the substrate, the channel being defined by a flowpath between an inlet and an outlet, the flowpath containing a plurality of tortuous path sections;
immobilizing a different receptor in each tortuous path section, one of the receptors being complementary to the analyte being tested for; and
flowing the sample, a conjugate solution, and an enzyme substrate sequentially through the continuous channel to perform an enzyme-linked immunosorbent assay on the sample.

26. The method of claim 25, further comprising the step of detecting the results of the assay.

27. A method of using a microfluidic chip to analyze a sample for multiple analytes, comprising:
providing a sample and a microfluidic chip, the chip comprising a substrate and a continuous channel in the substrate, the channel being defined by a flowpath between an inlet and an outlet, the flowpath containing a plurality of tortuous path sections;
including a different receptor in each tortuous path section, each receptor being complementary to an analyte; and
flowing the sample, a conjugate solution, and an enzyme substrate sequentially through the continuous channel to perform an enzyme-linked immunosorbent assay on the sample.

28. The method of claim 27, further comprising the step of detecting the results of the assay in each tortuous path section.

29. A method of using a microfluidic chip to analyze a sample for multiple analytes, comprising:
providing a sample and a microfluidic chip, the chip comprising a substrate and a plurality of continuous channels in the substrate, each continuous channel being defined by a flowpath between an inlet and an outlet, the flowpath comprising a plurality of tortuous path sections;
including a different receptor in each tortuous path section, each receptor being complementary to an analyte; and
flowing a portion of the sample through each continuous channel to perform an enzyme-linked immunosorbent assay on the portion of the sample being flowed through the channel, the sample being loaded into each channel by dipping one end of the microfluidic chip into a solution containing the sample.

30. The method of claim 29, further comprising the step of detecting the results of the assay in each tortuous path section.

31. A method of using a microfluidic chip to simultaneously analyze multiple samples for multiple analytes, comprising:
providing multiple samples and a microfluidic chip, the chip comprising a substrate and a plurality of continuous channels in the substrate, each continuous channel being defined by a flowpath between an inlet and an outlet, the flowpath including a plurality of tortuous path sections;
immobilizing a receptor complementary to an analyte in each tortuous path section; and
flowing a different sample through each continuous channel to simultaneously perform an enzyme-linked immunosorbent assay on each sample.

32. The method of claim 31, further comprising the step of detecting the results of the assay in each tortuous path section.

* * * * *

UNITED STATES PATENT AND TRADEMARK OFFICE
CERTIFICATE OF CORRECTION

PATENT NO.      : 8,075,854 B2
APPLICATION NO. : 11/937001
DATED           : December 13, 2011
INVENTOR(S)     : Yang et al.

It is certified that error appears in the above-identified patent and that said Letters Patent is hereby corrected as shown below:

Title page should read

Item (73) Assignees: The Ohio State University Research Foundation and
Bioprocessing Innovative Company Signed and Sealed this
Twenty-eighth Day of February, 2012

David J. Kappos
*Director of the United States Patent and Trademark Office*